United States Patent
Kono et al.

(10) Patent No.: US 10,359,778 B2
(45) Date of Patent: Jul. 23, 2019

(54) INDOOR MONITORING SYSTEM AND METHOD FOR STRUCTURE

(71) Applicant: MITSUBISHI HEAVY INDUSTRIES, LTD., Tokyo (JP)

(72) Inventors: Takayuki Kono, Tokyo (JP); Yoichiro Tsumura, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 174 days.

(21) Appl. No.: 15/322,230

(22) PCT Filed: Jan. 20, 2015

(86) PCT No.: PCT/JP2015/051360
§ 371 (c)(1),
(2) Date: Dec. 27, 2016

(87) PCT Pub. No.: WO2016/002236
PCT Pub. Date: Jan. 7, 2016

(65) Prior Publication Data
US 2017/0139410 A1 May 18, 2017

(30) Foreign Application Priority Data
Jul. 2, 2014 (JP) ................................. 2014-136868

(51) Int. Cl.
*B64C 39/02* (2006.01)
*B64D 47/08* (2006.01)
(Continued)

(52) U.S. Cl.
CPC ........... *G05D 1/0038* (2013.01); *B64D 47/08* (2013.01); *G01B 21/00* (2013.01); *G01C 3/08* (2013.01);
(Continued)

(58) Field of Classification Search
CPC .... G05D 1/0038; G05D 1/0094; B64D 47/08; G01C 21/206; G01C 3/08; G01C 23/00;
(Continued)

(56) References Cited

U.S. PATENT DOCUMENTS 8,060,270 B2   11/2011 Vian et al.
2009/0093907 A1*  4/2009 Masaki ................. G05D 1/024
                                                700/248

(Continued)

FOREIGN PATENT DOCUMENTS

CN        101044416      9/2007
CN        202600150     12/2012
(Continued)

OTHER PUBLICATIONS

Nikolic, Janosch, et al. "A UAV system for inspection of industrial facilities." IEEE Aerospace Conference (AERO 2013). IEEE, 2013. (Year: 2013).*

(Continued)

*Primary Examiner* — Alan D Hutchinson
(74) *Attorney, Agent, or Firm* — Wenderoth, Lind & Ponack, L.L.P.

(57) ABSTRACT

An indoor monitoring system for a structure comprises an unmanned floating machine provided with a propeller to float and move in the air inside a structure; a distance measuring unit on said machine to measures a distance between said machine and an inner wall surface of the structure; an inertial measurement unit on said machine to identify the attitude of the body of said machine; an image-capturing unit on said machine to capture an image of a structural body on the side of said machine; a control unit which controls said machine remotely; a flight position information acquiring unit which uses information from the distance measuring unit and the inertial measurement unit to (Continued)

acquire information relating to the current position of said machine; and a monitor unit which displays image information from the image-capturing unit and the position information from the flight position information acquiring unit.

20 Claims, 7 Drawing Sheets

(51) Int. Cl.
<table>
<tr><td>G01C 21/20</td><td>(2006.01)</td></tr>
<tr><td>G01C 23/00</td><td>(2006.01)</td></tr>
<tr><td>G01C 3/08</td><td>(2006.01)</td></tr>
<tr><td>G05D 1/00</td><td>(2006.01)</td></tr>
<tr><td>G01B 21/00</td><td>(2006.01)</td></tr>
<tr><td>G01C 15/00</td><td>(2006.01)</td></tr>
<tr><td>G01N 21/84</td><td>(2006.01)</td></tr>
</table>

(52) U.S. Cl.
CPC ........... *G01C 15/00* (2013.01); *G01C 21/206* (2013.01); *G01C 23/00* (2013.01); *G01N 21/84* (2013.01); *G05D 1/0094* (2013.01); *B64C 39/024* (2013.01); *B64C 2201/027* (2013.01); *B64C 2201/108* (2013.01); *B64C 2201/123* (2013.01); *B64C 2201/127* (2013.01); *B64C 2201/146* (2013.01)

(58) Field of Classification Search
CPC ........ G01C 15/00; G01N 21/84; G01B 21/00; B64C 2201/146; B64C 2201/123; B64C 39/024
See application file for complete search history.

(56) References Cited

U.S. PATENT DOCUMENTS

<table>
<tr><td>2010/0049391 A1</td><td>2/2010</td><td>Nakano</td></tr>
<tr><td>2011/0288696 A1</td><td>11/2011</td><td>Lefebure</td></tr>
<tr><td>2014/0061376 A1</td><td>3/2014</td><td>Fisher et al.</td></tr>
</table>

FOREIGN PATENT DOCUMENTS

<table>
<tr><td>CN</td><td>103365295</td><td>10/2013</td></tr>
<tr><td>CN</td><td>103455036</td><td>12/2013</td></tr>
<tr><td>CN</td><td>203342367</td><td>12/2013</td></tr>
<tr><td>CN</td><td>103697889</td><td>4/2014</td></tr>
<tr><td>EP</td><td>1 901 153</td><td>3/2008</td></tr>
<tr><td>JP</td><td>6-73922</td><td>3/1994</td></tr>
<tr><td>JP</td><td>2001-209426</td><td>8/2001</td></tr>
<tr><td>JP</td><td>2004-211995</td><td>7/2004</td></tr>
<tr><td>JP</td><td>2007-213190</td><td>8/2007</td></tr>
<tr><td>JP</td><td>2009-093308</td><td>4/2009</td></tr>
<tr><td>JP</td><td>2009-110250</td><td>5/2009</td></tr>
<tr><td>JP</td><td>2009-136987</td><td>6/2009</td></tr>
<tr><td>JP</td><td>2009-163156</td><td>7/2009</td></tr>
<tr><td>JP</td><td>2009-294713</td><td>12/2009</td></tr>
<tr><td>JP</td><td>2010-79869</td><td>4/2010</td></tr>
<tr><td>JP</td><td>2011-530692</td><td>12/2011</td></tr>
<tr><td>JP</td><td>2012-509812</td><td>4/2012</td></tr>
<tr><td>JP</td><td>2012-228944</td><td>11/2012</td></tr>
<tr><td>JP</td><td>2013-531573</td><td>8/2013</td></tr>
<tr><td>JP</td><td>2014-119828</td><td>6/2014</td></tr>
</table>

OTHER PUBLICATIONS

Shen, Shaojie, Nathan Michael, and Vijay Kumar. "Autonomous multi-floor indoor navigation with a computationally constrained MAV." Robotics and automation (ICRA), 2011 IEEE international conference on. IEEE, 2011. (Year: 2011).*
Strelow, Dennis, and Sanjiv Singh. "Motion estimation from image and inertial measurements." The International Journal of Robotics Research 23.12 (2004): 1157-1195. (Year: 2004).*
Extended European Search Report dated May 3, 2017 in corresponding European Application No. 15814504.5.
S. Shen et al., "Autonomous Multi-Floor Indoor Navigation with a Computationally Constrained MAV", 2011 IEEE International Conference on Robotics and Automation, May 2011, pp. 20-25.
J. Nikolic et al., "A UAV System for Inspection of Industrial Facilities", IEEEAC Paper #2301, Version 2, Mar. 2013, pp. 1-8.
International Search Report dated Apr. 21, 2015 in corresponding International Application No. PCT/JP2015/051360.
Seungho Jeong et al., "Vision-Based Localization of a Quad-Rotor System", Ubiquitous Robots and Ambient Intelligence (URAI), 2012 9th International Conference on, Nov. 26, 2012, pp. 636-638.
Evan Dill et al., "Seamless Indoor-Outdoor Navigation for Unmanned Multi-Sensor Aerial Platforms", Position, Location and Navigation Symposium—PLANS 2014, 2014 IEEE/ION, May 5, 2015, pp. 1174-1182.
Office Action dated Feb. 22, 2016 in Taiwanese Application No. 104102689 (with English translation).
Office Action dated Jul. 21, 2016 in Taiwanese Application No. 104102689 (with English translation).
Written Opinion of the International Searching Authority dated Apr. 21, 2015 in corresponding International Application No. PCT/JP2015/051360.
Decision of Patent Grant dated Dec. 15, 2016 in corresponding Taiwanese Application No. 104102689 (with English translation).
Office Action dated Jun. 12, 2018 in corresponding Japanese Application No. 2014-136868, with English translation.

* cited by examiner

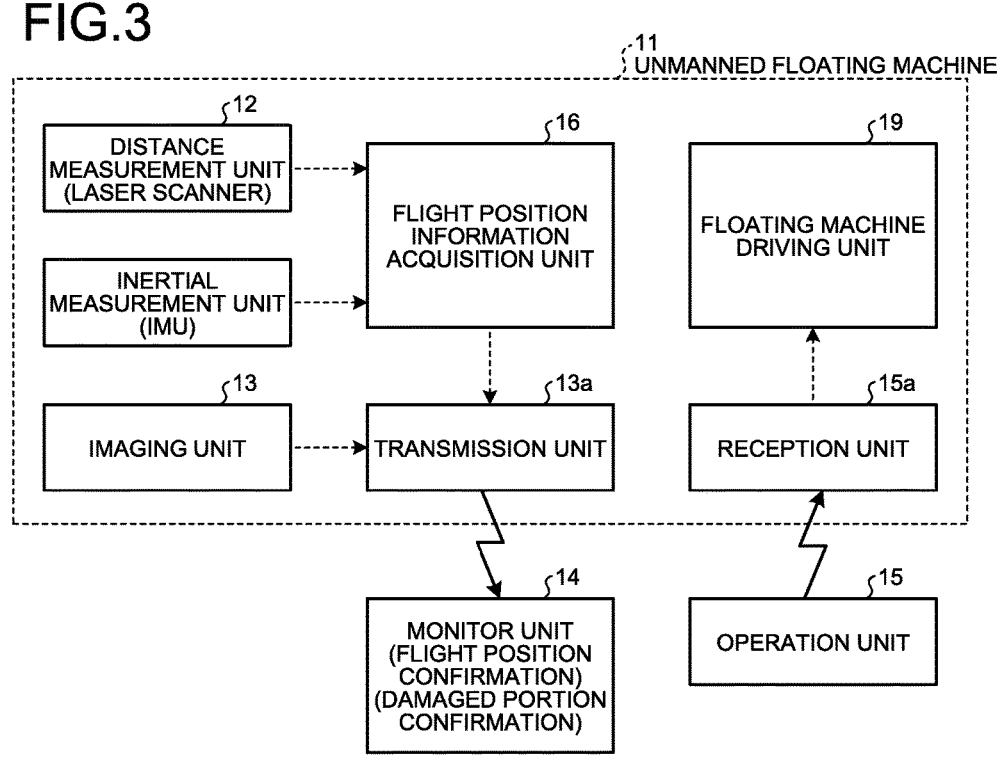
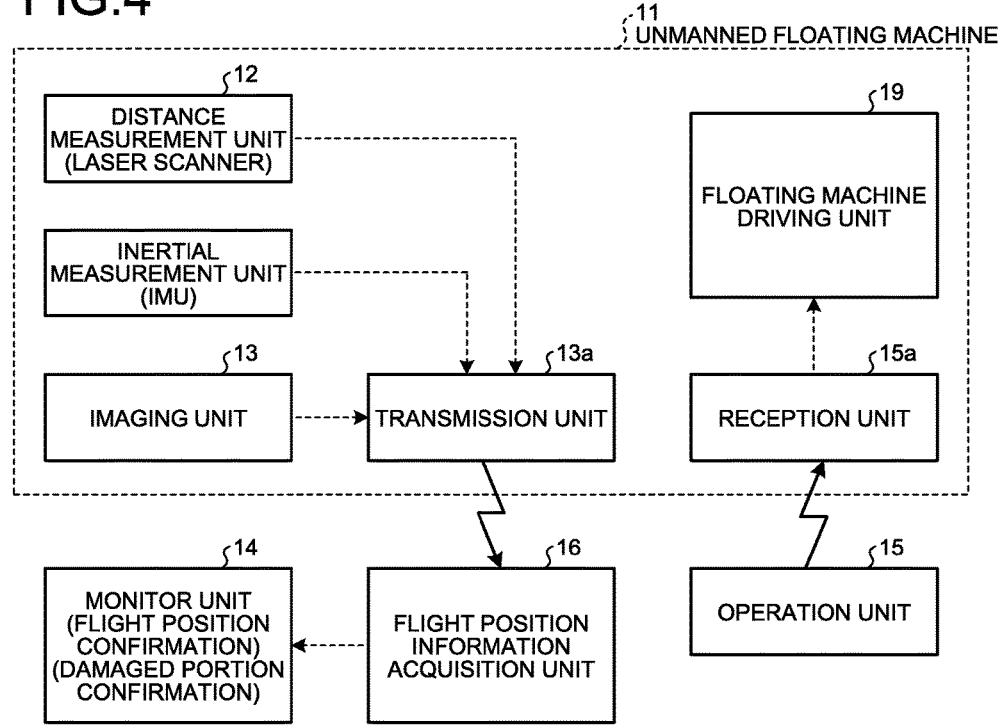

FIG.6
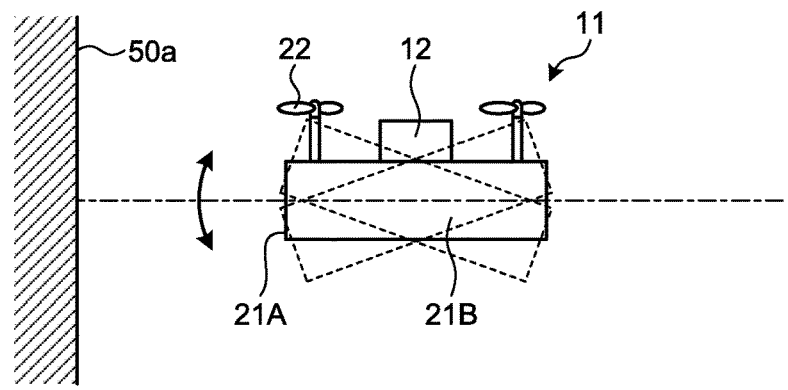
<PITCH($\theta$)>
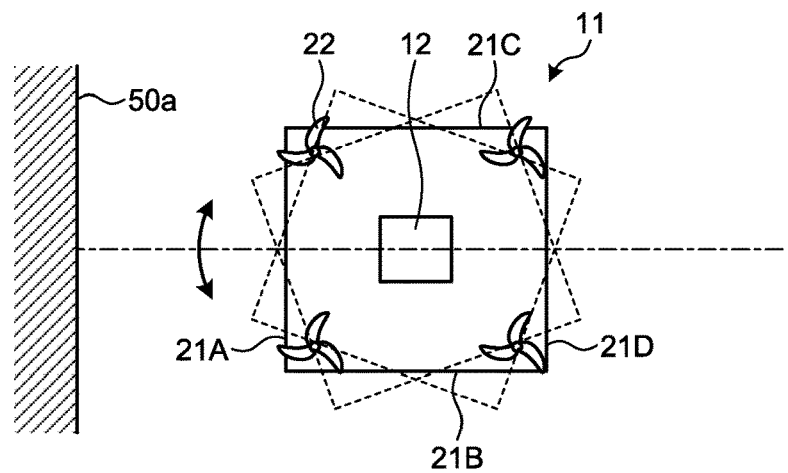
<YAW($\psi$)>
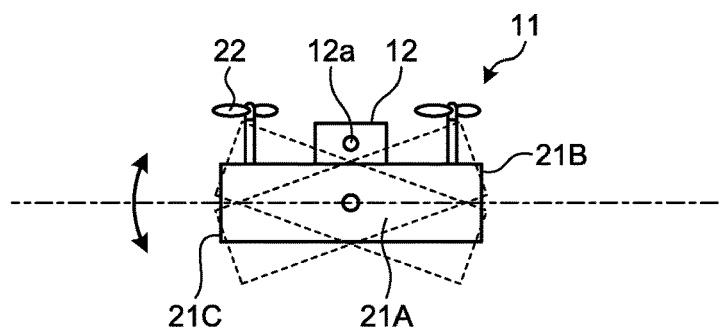
<ROLL($\phi$)>

INDOOR MONITORING SYSTEM AND METHOD FOR STRUCTURE

CROSS-REFERENCE TO RELATED APPLICATION

This application is a national stage of PCT International Application No. PCT/JP2015/051360, filed on Jan. 20, 2015, which claims priority to and incorporates by reference the entire contents of Japanese Patent Application No. 2014-136868 filed in Japan on Jul. 2, 2014.

FIELD

The present invention relates to an indoor monitoring system and method for a structure.

For example, a boiler furnace used at a thermal power plant needs to be opened during construction and periodically after starting operation so that a worker enters the inside to conduct maintenance inspection. During this maintenance inspection, it is necessary to define a portion to be inspected, but it is difficult to accurately grasp the portion to be inspected visually because the capacity of the boiler furnace is large. Thus, a height position and a lateral position of the portion to be inspected have been conventionally measured and marked using a measuring tape or the like to grasp where the worker is or a maintenance inspection position, but such a method requires not only erection of scaffolding for the worker and installation of a gondola but also a lot of efforts, cost, and inspection periods.

Thus, a technique has been conventionally proposed to clean up the inside of a structure such as a stack using an unmanned inspection apparatus (Japanese Laid-open Patent Publication No. 6-73922). However, this proposal also requires a cradle to install a wire, and efforts, cost and inspection periods are required for the preparation thereof.

In addition, application of an unmanned inspection technique, which does not require erection of scaffolding using an unmanned aircraft and GPS (Global Positioning System), has been proposed for an outdoor structure (Japanese Patent Application National Publication (Laid-Open) No. 2011-530692).

However, since electric waves from satellites do not reach indoor structures such as the inside of a boiler and a stack, it is difficult to obtain a flight position using the GPS and to stably maneuver the unmanned aircraft. Thus it is difficult to use the existing inspection technique using the unmanned aircraft.

In this regard, a system in which indoor flight without using a GPS is possible has been also proposed (EP 1901153 A).

However, a characteristic point (or a pattern) needs to be provided on the ground instead of the GPS in the proposal of Patent Literature 3, and there is a problem that a place where this characteristic point (or the pattern) can be installed is limited. In addition, since the structure such as the boiler furnace and the stack has a closed space whose inside is dark, there is a problem that it is difficult to confirm the characteristic point.

Accordingly, there has been a request for emergence of an indoor monitoring system for a structure that is capable of unmanned inspection which reliably obtains internal position information in a closed indoor structure such as a boiler furnace and a stack and also capable of reducing efforts, cost, inspection periods by omitting erection of scaffolding, for example.

SUMMARY

It is an object of the present disclosure to at least partially solve the problems in the conventional technology.

According to one aspect, there is provided an indoor monitoring system for a structure comprising: an unmanned floating machine including a floating means which levitates the unmanned floating machine inside the structure by remote control; a distance measurement unit which is mounted to the unmanned floating machine and configured to measure a distance between the unmanned floating machine and an inner wall surface of the structure; an inertial measurement unit which is mounted to the unmanned floating machine and configured to obtain an attitude of a body of the unmanned floating machine; an imaging unit which is mounted to the unmanned floating machine and configured to image a structural body on the wall surface side of the structure; an operation unit which is configured to remotely control the unmanned floating machine; a flight position information acquisition unit which is configured to acquire current position information of the unmanned floating machine based on information from the distance measurement unit and information from the inertial measurement unit; and a monitor unit which is configured to display image information from the imaging unit and position information from the flight position information acquisition unit, wherein the flight position information acquisition unit is further configured to execute a horizontal-direction distance measuring step of measuring horizontal distance information between the unmanned floating machine and the inner wall surface of the structure using the distance measurement unit, an attitude angle acquiring step of acquiring an attitude angle of the unmanned floating machine using the inertial measurement unit, a horizontal-direction distance correcting step of correcting the horizontal distance information using the attitude angle acquired in the attitude angle acquiring step, a horizontal-direction distance acquiring step of acquiring distances between the inner wall surface of the structure and the unmanned floating machine in at least two different horizontal directions around the unmanned floating machine based on a yaw angle acquired by the inertial measurement unit, and a horizontal-direction current position information acquiring step of acquiring current position information in a horizontal direction from existing horizontal cross-sectional shape information of the structure.

According to one aspect, there is provided a An indoor monitoring method for a structure which uses an unmanned floating machine including a floating means which levitates the unmanned floating machine inside the structure by remote control, the method comprising: a distance measurement step executed in the unmanned floating machine and measuring a distance between the unmanned floating machine and an inner wall surface of the structure; an inertial measurement step executed in the unmanned floating machine and obtaining an attitude of a body of the unmanned floating machine; an imaging step executed in the unmanned floating machine and imaging a structural body on the wall surface side of the structure; an operation step of remotely controlling the unmanned floating machine; a flight position information acquisition step of acquiring current position information of the unmanned floating machine based on information from the distance measurement step and information from the inertial measurement step; and a monitor displaying step of displaying image information from the imaging step and position information from the flight position information acquisition step, wherein in the flight position information acquisition step, a horizontal-direction distance measuring step of measuring horizontal distance information between the unmanned floating machine and the inner wall surface of the structure by the distance measurement step is executed, an attitude angle acquiring step of acquiring an attitude angle of the unmanned floating machine by the inertial measurement step is executed, a horizontal-direction distance correcting step of correcting the horizontal distance information using the attitude angle acquired in the attitude angle acquiring step is executed, a horizontal-direction distance acquiring step of acquiring distances between the inner wall surface of the structure and the unmanned floating machine in at least two different horizontal directions around the unmanned floating machine based on a yaw angle acquired in the inertial measurement step is executed, and a horizontal-direction current position information acquiring step of acquiring current position information in a horizontal direction from existing horizontal cross-sectional shape information of the structure is executed.

According to one aspect, there is provided an indoor monitoring system for a structure comprising: an unmanned floating machine including a floating means which levitates the unmanned floating machine inside the structure by remote control; a distance measurement unit which is mounted to the unmanned floating machine and configured to measure a distance between the unmanned floating machine and an inner wall surface of the structure; an inertial measurement unit which is mounted to the unmanned floating machine and configured to obtain an attitude of a body of the unmanned floating machine; an imaging unit which is mounted to the unmanned floating machine and configured to image a structural body on the wall surface side of the structure; an operation unit which is configured to remotely control the unmanned floating machine; a flight position information acquisition unit which is configured to acquire current position information of the unmanned floating machine based on information from the distance measurement unit and information from the inertial measurement unit; and a monitor unit which is configured to display image information from the imaging unit and position information from the flight position information acquisition unit, wherein the flight position information acquisition unit is further configured to execute a horizontal-direction distance measuring step of measuring horizontal distance information between the unmanned floating machine and the inner wall surface of the structure using the distance measurement unit, when the unmanned floating machine is controlled inside the structure by the remote control to turn along the inner wall surface of the structure after rising by a predetermined distance repeatedly till the unmanned floating machine arrives at a predetermined height, an attitude angle acquiring step of acquiring an attitude angle of the unmanned floating machine using the inertial measurement unit, a horizontal-direction distance correcting step of correcting the horizontal distance information using the attitude angle acquired in the attitude angle acquiring step, a horizontal-direction distance acquiring step of acquiring distances between the inner wall surface of the structure and the unmanned floating machine based on a yaw angle acquired by the inertial measurement unit, and a horizontal-direction current position information acquiring step of acquiring current position information in a horizontal direction from existing horizontal cross-sectional shape information of the structure.

According to one aspect, there is provided an indoor monitoring method for a structure which uses an unmanned floating machine including a floating means which levitates the unmanned floating machine inside the structure by remote control, the method comprising: a distance measurement step executed in the unmanned floating machine and measuring a distance between the unmanned floating machine and an inner wall surface of the structure; an inertial measurement step executed in the unmanned floating machine and obtaining an attitude of a body of the unmanned floating machine; an imaging step executed in the unmanned floating machine and imaging a structural body on the wall surface side of the structure; an operation step of remotely controlling the unmanned floating machine; a flight position information acquisition step of acquiring current position information of the unmanned floating machine based on information from the distance measurement step and information from the inertial measurement step; and a monitor displaying step of displaying image information from the imaging step and position information from the flight position information acquisition step, wherein in the flight position information acquisition step, a horizontal-direction distance measuring step of measuring horizontal distance information between the unmanned floating machine and the inner wall surface of the structure is executed using the distance measurement step, when the unmanned floating machine is controlled inside the structure by the remote control to turn along the inner wall surface of the structure after rising by a predetermined distance repeatedly till the unmanned floating machine arrives at a predetermined height, an attitude angle acquiring step of acquiring an attitude angle of the unmanned floating machine is executed using the inertial measurement step, a horizontal-direction distance correcting step of correcting the horizontal distance information using the attitude angle acquired in the attitude angle acquiring step is executed, a horizontal-direction distance acquiring step of acquiring distances between the inner wall surface of the structure and the unmanned floating machine based on a yaw angle acquired in the inertial measurement step is executed, and a horizontal-direction current position information acquiring step of acquiring current position information in a horizontal direction from existing horizontal cross-sectional shape information of the structure is executed.

The above and other objects, features, advantages and technical and industrial significance of this disclosure will be better understood by reading the following detailed description of presently preferred embodiments of the disclosure, when considered in connection with the accompanying drawings.

According to the present invention, it is possible to perform the unmanned inspection which reliably obtains the position information inside the structure, for example, the boiler furnace, the stack, or the like, and it is also possible to achieve the significant reduction of efforts, cost, inspection periods by omitting the scaffolding erection, for example.

BRIEF DESCRIPTION OF THE DRAWINGS

FIG. 3 is a block configuration diagram of an indoor monitoring system for a structure according to the first embodiment.

FIG. 4 is a block configuration diagram of another indoor monitoring system for a structure according to the first embodiment.

FIG. 6 is a diagram illustrating three aspects of an attitude position of the unmanned floating machine according to the first embodiment.

DETAILED DESCRIPTION OF THE PREFERRED EMBODIMENTS

Hereinafter, preferred embodiments of the present invention will be described in detail with reference to the drawings. Incidentally, the present invention is not limited by the embodiments, and further, encompasses any configuration obtained by combining the respective embodiments when there are a plurality of embodiments.

First Embodiment

Figure 1:
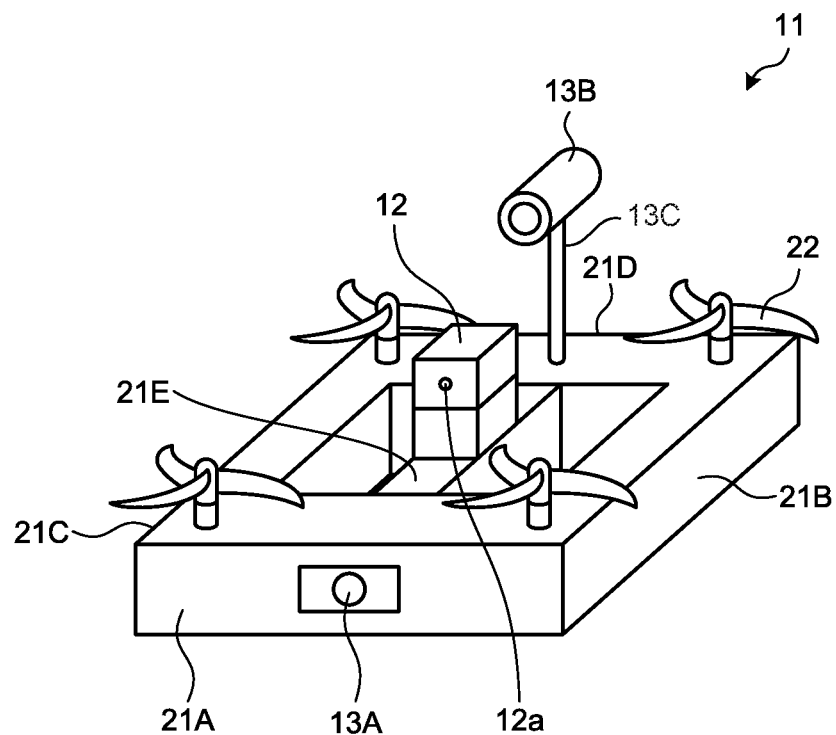
FIG. 1 is a schematic view of an unmanned floating machine according to a first embodiment.
Figure 2:
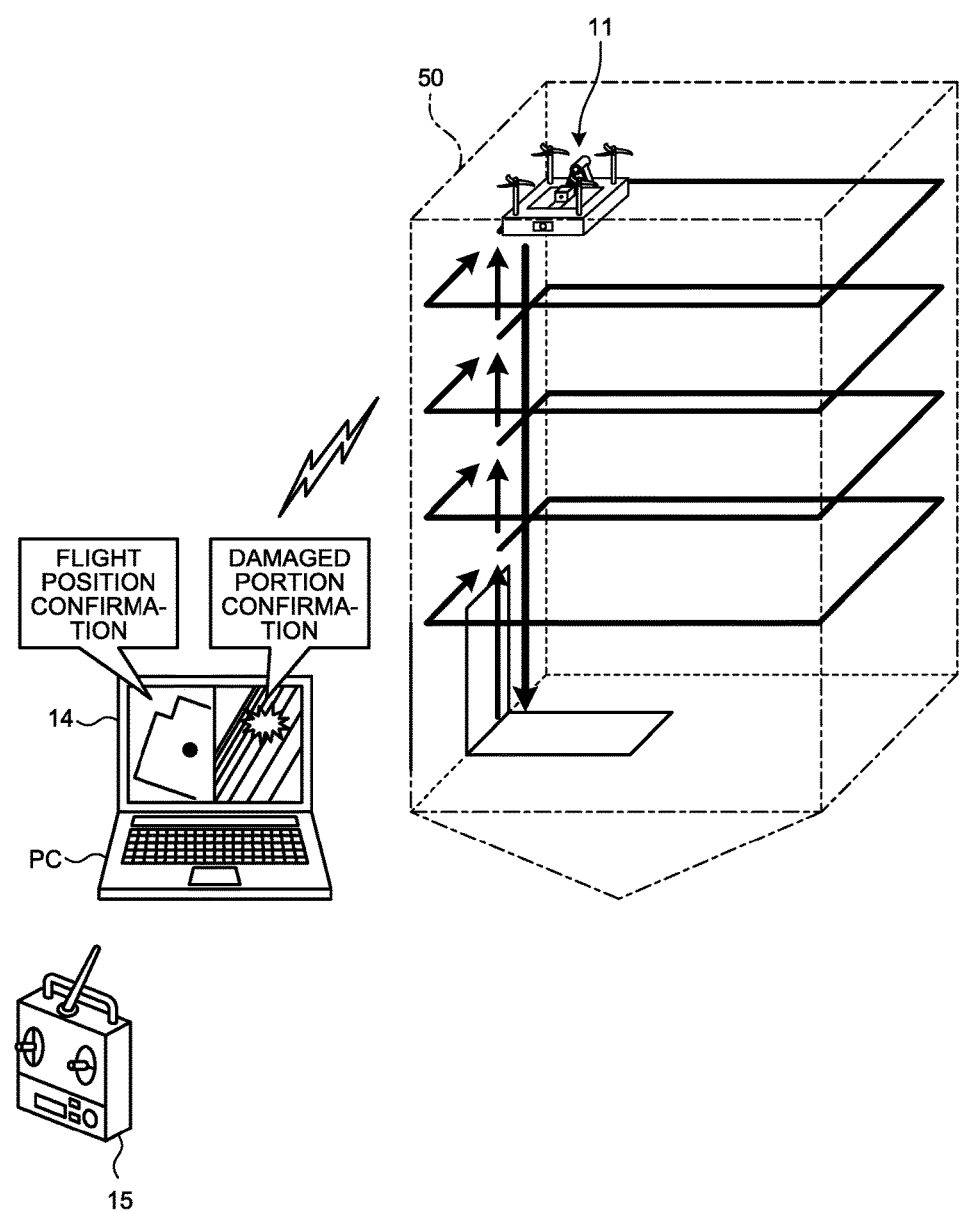
FIG. 2 is a schematic view illustrating an aspect of inspection of a boiler furnace according to the first embodiment.

FIG. 1 is a schematic view of an indoor monitoring system for a structure according to a first embodiment. FIG. 2 is a schematic view illustrating an aspect of inspection of a boiler furnace according to the first embodiment. FIG. 3 is a block configuration diagram of an indoor monitoring system for a structure according to the first embodiment. As illustrated in FIGS. 1 to 3, the indoor monitoring system for the structure according to the present embodiment is provided with: an unmanned floating machine 11 with propellers 22, for example, as a floating means which levitates and moves the unmanned floating machine inside a closed structure 50, for example, a boiler furnace or the like by remote control; a distance measurement unit (for example, a laser scanner, an ultrasonic sensor, or the like) 12 which is mounted to the unmanned floating machine 11 and measures a distance between the unmanned floating machine 11 and an inner wall surface of the structure 50; an inertial measurement unit (IMU) which is mounted to the unmanned floating machine 11 and obtains an attitude of a body of the unmanned floating machine; an imaging unit (a still image imaging unit 13A and a video imaging unit 13B) 13 which is mounted to the unmanned floating machine 11 and images a structure (for example, piping, fitting or the like) on a wall surface side of the structure 50; an operation unit 15 which remotely controls the unmanned floating machine 11; a flight position information acquisition unit 16 which acquires current position information of the unmanned floating machine 11 based on information (signal) of the distance measurement unit 12 and information (signal) of the inertial measurement unit; and a monitor unit 14 which displays image information from the imaging unit 13 and position information from the flight position information acquisition unit 16. Incidentally, 12a represents a laser light emitting portion.

Further, the flight position information acquisition unit 16 is configured to execute: a distance measuring step (step 1: S-1) of measuring a horizontal distance information $(r(t),\alpha_s)$ between the unmanned floating machine 11 and the inner wall surface of the structure 50 using the distance measurement unit 12; an attitude angle acquiring step (step 2: S-2) of acquiring an attitude angle of the unmanned floating machine 11 using the inertial measurement unit; a distance correcting step (step 3: S-3) of correcting the horizontal distance information $(r(t),\alpha_s)$ using the attitude angle acquired in step 2; a distance acquiring step (step 4: S-4) of acquiring distances of at least two points (any two points among front $(L_f(t))$ and left $(L_L(t))$, front $(L_f(t))$ and right $(L_R(t))$, back $(L_B(t))$ and left $(L_L(t))$, and back $(L_B(t))$ and right $(L_R(t))$) on the front, back, right and left of the unmanned floating machine 11 on the basis of a yaw angle acquired by the inertial measurement unit; and a horizontal-direction current position information acquiring step (step 5: S-5) of acquiring current position information in the horizontal direction from existing horizontal cross-sectional shape information of the structure 50.

In the present embodiment, the structure 50, which has a simple shape (whose cross-sectional shape is a rectangle or a circle), for example, a boiler furnace, a stack, or the like, is set as a target of inspection. Since the inside of the structure 50 is the target, provided is a system that monitors a flight position (current flight position information) of the unmanned floating machine 11 using the distance measurement unit (for example, the laser scanner, the ultrasonic sensor, or the like) 12 which does not use a GPS and the inertial measurement unit (IMU) which belongs a sensor group used for attitude control of the unmanned floating machine 11.

In the present embodiment, the unmanned floating machine 11 is operated by the operation unit 15 while confirming the flight position of the unmanned floating machine 11 and an image (a damaged portion) using the monitor unit 14 of a personal computer PC in a ground station positioned outside the closed structure (boiler furnace) 50, thereby performing inspection of an inner wall of a closed space of the boiler furnace 50, as illustrated in FIG. 2.

During the inspection, the unmanned floating machine 11 is introduced from an entrance of the boiler furnace 50 illustrated in FIG. 2, thereafter is raised by a predetermined distance inside the boiler furnace 50, and is turned along inner surfaces of walls in the four directions by operating the operation unit 15 on the ground side. Thereafter, the unmanned floating machine 11 is raised again by a predetermined distance, and is turned along the inner wall surfaces in the four directions in the same manner. This operation is repeated until the top of the boiler furnace 50 is inspected, and then, the unmanned floating machine 11 is lowered, thereby ending the inspection.

A degree of damage such as a crack in the piping on the inner surface is inspected using the imaging unit. During this inspection, it is possible to confirm the flight position and the damaged portion of the closed indoor structure on the monitor unit 14 according to the present embodiment, and thus, it is possible to perform unmanned inspection that reliably obtains the internal position information.

The perimeter of the unmanned floating machine 11 is protected by an body guard portion 21 (a front-side guard portion 21A, a left-side guard portion 21B, a right-side guard portion 21C, and a back-side guard portion 21D), and there is provided the propeller 22 as the floating means on each upper surface of four corners of the body guard portion 21, the distance measurement unit 12 mounted at a center portion of a body 21E, the still image imaging unit 13A positioned on a part of the front-side guard portion 21A, and the video imaging unit 13B positioned on the back-side guard portion 21D via a support portion 13C, as illustrated in FIG. 1. Incidentally, the distance measurement unit 12 scans a predetermined angle (±135° in the present embodiment) and can be turned by a turning means (not illustrated).

Here, any one of the still image imaging unit 13A and the video imaging unit 13B may be used as the imaging unit 13 to confirm the internal information.

Hereinafter, a description will be given regarding procedure of position monitoring in a case where the laser scanner is used as the distance measurement unit 12 in the present embodiment.

<Monitoring in Horizontal Direction>

(1) First, a distance $(r(t),\alpha_s)$ is acquired by the distance measurement unit 12 to implement monitoring in the horizontal direction.

Figure 5:
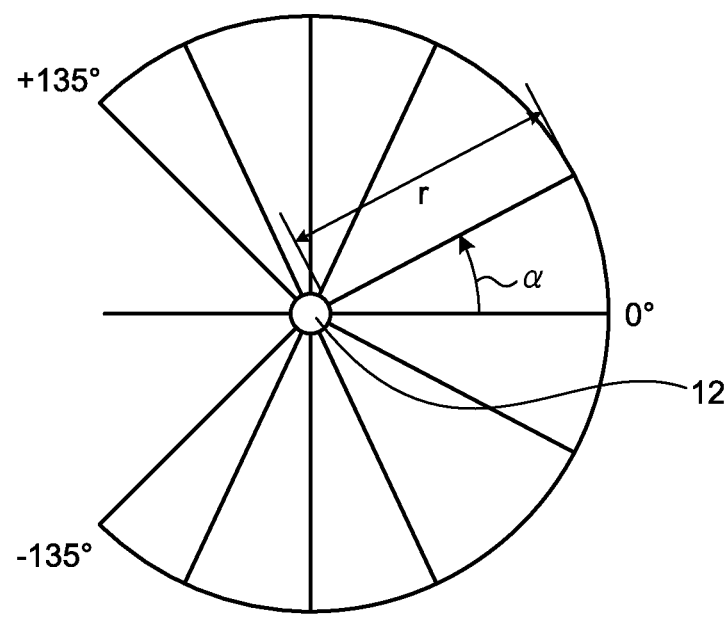
FIG. 5 is a diagram illustrating an example of a scan range in a case where a laser scanner is used as a distance measurement unit according to the first embodiment.

Here, FIG. 5 illustrates an example of a scan range of the laser scanner. In the present embodiment, a scanner-type range sensor, "UTM-30 LX (product name)" manufactured by HOKUYO AUTOMATIC CO., LTD. is used.

As illustrated in FIG. 5, this scanner-type range sensor is a two-dimensional scanning-type optical distance sensor, which measures a distance to an object to be inspected while performing scanning with laser light, and a scan angle is ±135° with 0° as the center thereof.

In FIG. 5, a distance (r) is an actually measured distance obtained when measurement is performed up to an inner wall 50a from the laser scanner of the distance measurement unit 12, and α is an angle at the measured scanning step thereof. A scanning step (s) for measurement in this device is set to every 0.25°.

(2) Next, attitude angles including a pitch angle ($\theta(t)$), a yaw angle ($\psi(t)$), a roll angle ($\varphi(t)$) of the unmanned floating machine 11 are acquired by the inertial measurement unit (IMU).

FIG. 6 is a diagram illustrating three aspects of an attitude position of the unmanned floating machine according to the first embodiment.

The inertial measurement unit (IMU) is a device that detects angles (or angular velocities) and accelerations in three axes governing a motion.

Here, the upper stage of FIG. 6 illustrates an aspect of vertical rotation of the unmanned floating machine 11 which is turning (the pitch (θ)) where the front-side guard portion 21A (on a nose side) facing the inner wall 50a side is raised or lowered. The middle stage of FIG. 6 illustrates an aspect of horizontal rotation of the body of the unmanned floating machine 11 which is turning (the yaw (ψ)) where a direction of a nose is shifted right and left, and the left-side guard portion 21B and the right-side guard portion 21C swing right and left. The lower stage of FIG. 6 is an aspect of rotation about an axis in a travel direction of the unmanned floating machine 11 which is turning (the roll (φ)) where the body is tilted right and left. Incidentally, the right and left of the body are based on the travel direction thereof.

Next, a position monitoring measuring step will be described with reference to FIG. 3.

The flight position information acquisition unit 16 is configured to obtain a real distance based on actual distance information of the distance measurement unit 12 and the attitude angle information of the inertial measurement unit (IMU). This is because there is a need for correction of the measured distance since the unmanned floating machine 11 is not always capable of flying constantly according to XY coordinates.

Figure 7:
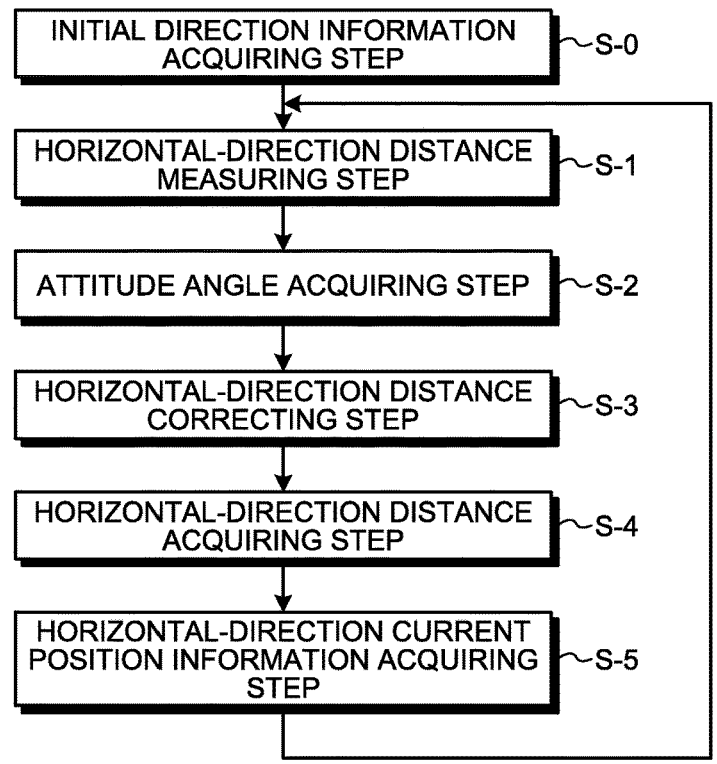
FIG. 7 is a flowchart of position monitoring in the horizontal direction according to the first embodiment.

FIG. 7 is a flowchart of position monitoring in the horizontal direction according to the first embodiment.

The measurement in the horizontal direction is performed through step 1 (S-1) to step 5 (S-5).

Prior to this measurement, an initial direction information acquiring step (S-0) of acquiring initial direction information, obtained when the unmanned floating machine 11 is positioned at the bottom inside the structure 50, is provided in the present embodiment, but this step may be omitted.

1) Step 1 is the horizontal-direction distance measuring step (S-1) of measuring the horizontal distance information $(r(t),\alpha_s)$ between the unmanned floating machine 11 and the inner wall 50a of the structure 50 using the distance measurement unit 12.

2) Step 2 is the attitude angle acquiring step (S-2) of acquiring the attitude angle of the unmanned floating machine 11 using the inertial measurement unit (IMU).

3) Step 3 is a horizontal-direction distance correcting step (S-3) of correcting the horizontal distance information $(r(t), \alpha_s)$ using the attitude angle acquired in step 2 (S-2).

Figure 9:
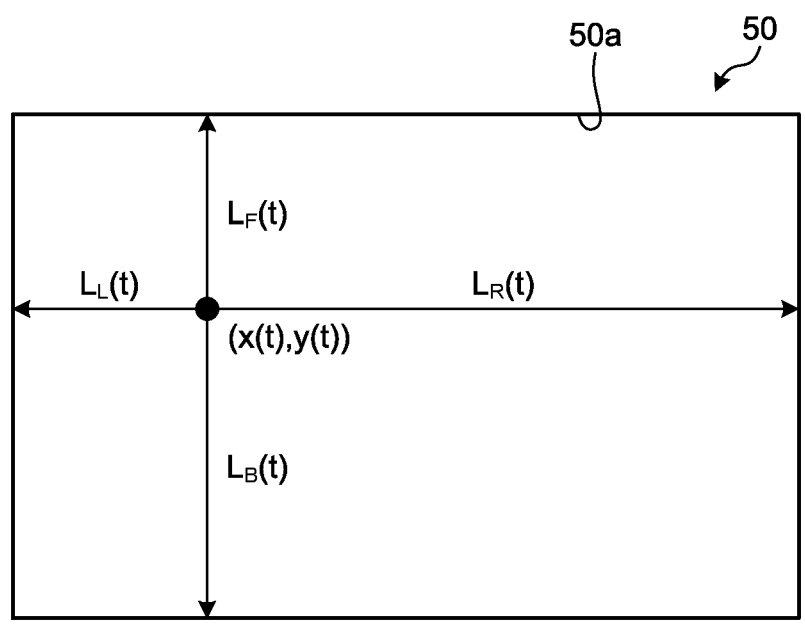
FIG. 9 is a diagram illustrating an example of acquisition of a current position in the horizontal direction according to the first embodiment.

4) Step 4 is a horizontal-direction distance acquiring step (S-4) of acquiring distances of at least two points (any two points among front ($L_F(t)$) and left ($L_L(t)$), front ($L_F(t)$) and right ($L_R(t)$), back ($L_B(t)$) and left ($L_L(t)$), and back ($L_B(t)$) and right ($L_R(t)$)) on the front, back, right and left of the unmanned floating machine 11 on the basis of the yaw angle (ψ) acquired by the inertial measurement unit (IMU), as illustrated in FIG. 9.

5) Step 5 is the horizontal-direction current position information acquiring step (S-5) of acquiring the current position information in the horizontal direction from the existing horizontal cross-sectional shape information of the structure 50.

It is possible to acquire the real distance information in the horizontal direction on consideration of the attitude angle at the time of measurement of the unmanned floating machine 11 by executing step 1 (S-1) to step 5 (S-5).

Here, the correction of the measured distance using the attitude angle acquired in step 3 (S-3) is performed as follows.

A laser measurement point obtained as $(r(t),\alpha_s)$ is transformed into coordinates $(x_R, y_R)$. This coordinate transformation is obtained by the following Formula (1).

$$\begin{pmatrix} x_R(t) \\ y_R(t) \end{pmatrix} = \begin{pmatrix} r(t)\cos\alpha_s \\ r(t)\sin\alpha_s \end{pmatrix} \quad (1)$$

Transformation of a corrected measurement point (x'(t), y'(t)) into a rotation coordinate system is obtained by the following Formula (2).

$$\begin{pmatrix} x'(t) \\ y'(t) \\ z'(t) \\ 1 \end{pmatrix} = \begin{pmatrix} 1 & 0 & 0 & 0 \\ 0 & \cos\theta(t) & -\sin\theta(t) & 0 \\ 0 & \sin\theta(t) & \cos\theta(t) & 0 \\ 0 & 0 & 0 & 1 \end{pmatrix} \begin{pmatrix} \cos\phi(t) & 0 & \sin\phi(t) & 0 \\ 0 & 1 & 0 & 0 \\ -\sin\phi(t) & 0 & \cos\phi(t) & 0 \\ 0 & 0 & 0 & 1 \end{pmatrix} \begin{pmatrix} x_R(t) \\ y_R(t) \\ z \\ 1 \end{pmatrix} \quad (2)$$

A value obtained from Formula (2) is transformed into a coordinate system (r,α) of laser measurement. This coordinate transformation is obtained by the following Formula (3).

$$\begin{pmatrix} r'(t) \\ \alpha'(t) \end{pmatrix} = \begin{pmatrix} \sqrt{x^2 + y^2} \\ \arctan(y/x) \end{pmatrix} \quad (3)$$

Next, each distance on the front, back, right and left of the unmanned floating machine 11 is obtained on the basis of the yaw angle $\psi$ (t) acquired by the inertial measurement unit (IMU) in step 4 (S-4). However, when a scan angle is out of a predetermined scan range, the obtained data is not employed as a distance from a wall side.

Scan angle data where a scan angle $\alpha_1=\psi$ (t) is set as a front distance $L_F(t)$.

Scan angle where a scan angle $\alpha_2=\psi$ (t)−90° is set as a left distance $L_L(t)$.

Scan angle where a scan angle $\alpha_3=\psi$ (t)+90° is set as a right distance $L_R(t)$.

Scan angle where a scan angle $\alpha_4=\psi(t)+180°$ is set as a back distance $L_B(t)$.

In the final step 5 (S-5), a current position (x(t),y(t)) is acquired from the existing horizontal cross-sectional shape using measurable distances (at least two of the front, back, right and left distance).

Accordingly, it is possible to acquire the real current position, and it is possible to confirm the imaging information imaged in this current position and the position information by the monitor unit 14.

When this measurement of the position information is performed every time when the unmanned floating machine 11 travels, it is possible to reliably obtaining the position information continuously.

<Monitoring in Height Direction>

Figure 8:
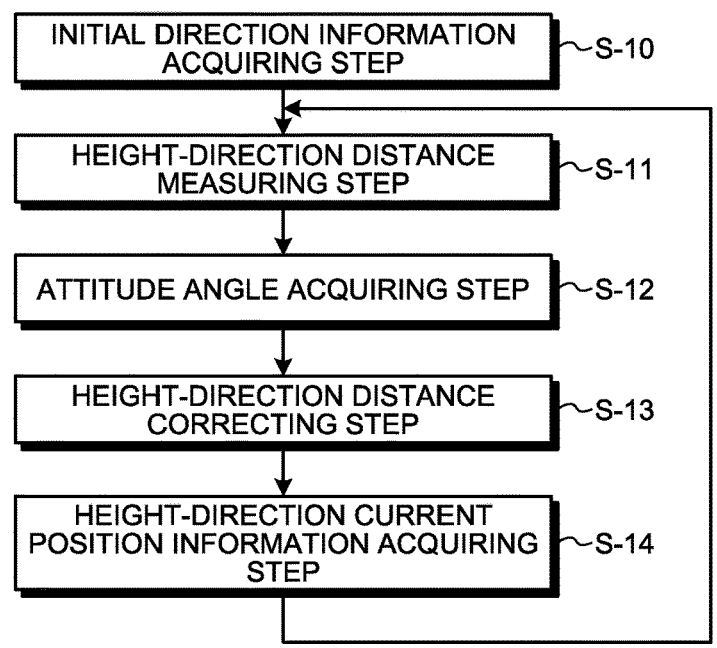
FIG. 8 is a flowchart of position monitoring in the height direction according to the first embodiment.

FIG. 8 is a flowchart of position monitoring in the height direction according to the first embodiment.

An initial direction information acquiring step (S-10) of acquiring an initial direction information uses the information obtained in the initial direction information acquiring step (S-0) of acquiring the initial direction information in the horizontal direction.

The measurement in the height direction is performed through the following step 11 (S-11) to step 14 (S-14).

6) Step 11 is a height-direction distance measuring step (S-11) of measuring the distance information $(L_D(t),\alpha_S)$ between the unmanned floating machine 11 and the structure 50 on the lower side in the height direction using the distance measurement unit 12.

Here, the measurement in the height direction using laser light is performed using a reflective optical system such as a mirror (not illustrated). When an irradiation distance of the laser light does not reach as the unmanned floating machine 11 is raised, distance information $(L_U(t),\alpha_S)$ on the upper side may be measured by causing the laser light to be reflected to the upper side.

7) Step 12 is an attitude angle acquiring step (S-12) of acquiring an attitude angle of the unmanned floating machine 11 using the inertial measurement unit (IMU).

8) Step 13 is a height-direction distance correcting step (S-13) of correcting the distance information $(L_D(t))$ in the height direction using an attitude angle $(\varphi(t),\theta(t))$ acquired in step 12 (S-12).

9) Step 14 is a height-direction current position information acquiring step (S-14) of acquiring current position information in the height direction from existing vertical cross-sectional shape information of the structure 50.

In the correction in step 13 (S-13), a corrected measurement point (z'(t)) is obtained from the following Formula (4).

$$z'=z\cos\alpha\cos\beta \qquad (4)$$

Therefore, it is possible to transform the actually measured distances in the horizontal direction and the height direction into the real distances and to reliably acquire the position information.

As a result, it is possible to perform the inspection that reliably obtains the measurement position using the unmanned floating machine inside the structure 50 where it is difficult to use the GPS. As a result, it is unnecessary to erect scaffolding inside the structure 50 as in the related art, and it is possible to significantly reduce efforts, cost, and inspection periods for internal inspection.

FIG. 3 is a block configuration diagram of an indoor monitoring system for a structure according to the first embodiment. FIG. 4 is a block configuration diagram of another indoor monitoring system for a structure according to the first embodiment.

As illustrated in FIG. 3, the present embodiment is a case in which position information processing is executed on the unmanned floating machine 11 side.

In the present embodiment, the flight position information acquisition unit 16 is mounted at a predetermined portion (not illustrated) on the unmanned floating machine 11 side, and here, acquires real current position information and transmits the acquired real current position information to the ground side by a transmission unit 13a to display the information on the monitor unit 14.

Incidentally, the operation of the unmanned floating machine 11 is performed in such a manner that a reception unit 15a receives a signal from the operation unit 15 and a flight command is issued to a floating machine driving unit 19.

In addition, the imaging information of the imaging unit 13 (the still image imaging unit 13A and the video imaging unit 13B) 13 is transmitted to the ground side by the transmission unit 13a at the same time and displayed on the monitor unit 14 in the present embodiment.

With respect to this, another example illustrated in FIG. 4 is a case in which the position information processing is performed on a controller terminal side of the personal computer PC on the ground.

In this example, the flight position information acquisition unit 16 is mounted to the controller terminal of the PC on the ground side (base station), and information (signal) of the distance measurement unit 12 and information (signal) of the inertial measurement unit (IMU) are transmitted to the ground side by the transmission unit 13a. Further, the received information is processed by the flight position information acquisition unit 16 to acquire real current position information, and this acquired current position information is displayed on the monitor unit 14.

Although the imaging information imaged by the imaging unit 13 is transmitted by the transmission unit 13a in the present embodiment, the present invention is not limited thereto, and for example, may be configured such that the imaging information is temporarily stored in a memory unit of the imaging unit on the unmanned floating machine 11 side, the information is transmitted to the ground station side after ending measurement, and the imaging information and the position information are processed to match each other.

As described above, it is possible to perform the unmanned inspection which reliably obtains the position information inside the structure 50, for example, the boiler furnace, the stack, or the like, and it is possible to achieve the significant reduction of efforts, cost, inspection periods by omitting erection of scaffolding, for example, according to the present embodiment.

Second Embodiment

Although the measurement of the distance measurement unit 12 is performed to obtain the information of the single point in the first embodiment, the present invention is not limited thereto, and the accuracy in position measurement may be improved based on measurement information at multiple points.

That is, multiple points are extracted and averaged based on the scan angle in the distance measurement unit 12 to obtain each distance in the calculation of distances in the horizontal direction and the height direction. Further, when more than half of the multiple points is abnormal for distance measurement or unmeasurable, such points are not used for the position monitoring.

As a result, it is possible to reduce influence of a distance acquisition error.

The present disclosure has been made in view of the above-described problems, and an object thereof is to provide an indoor monitoring system and method for a structure that is capable of unmanned inspection which reliably obtains internal position information, and also capable of reducing efforts, cost, inspection periods by omitting erection of scaffolding, for example.

Although this disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

The invention claimed is:

1. An indoor monitoring system for a structure comprising:
    an unmanned floating machine including a floating means which levitates the unmanned floating machine inside the structure by remote control;
    a distance measurement unit which is mounted to the unmanned floating machine and configured to measure a distance between the unmanned floating machine and an inner wall surface of the structure;
    an inertial measurement unit which is mounted to the unmanned floating machine and configured to obtain a pitch angle and a roll angle of the unmanned floating machine;
    an imaging unit which is mounted to the unmanned floating machine and configured to image a structural body on the wall surface side of the structure;
    an operation unit which is configured to remotely control the unmanned floating machine;
    a flight position information acquisition unit which is configured to acquire current position information of the unmanned floating machine based on information from the distance measurement unit and information from the inertial measurement unit; and
    a monitor unit which is configured to display image information from the imaging unit and position information from the flight position information acquisition unit,
    wherein the flight position information acquisition unit is further configured to execute
    a horizontal-direction distance measuring step of measuring horizontal distance information between the unmanned floating machine and the inner wall surface of the structure using the distance measurement unit,
    a pitch angle and a roll angle acquiring step of acquiring the pitch angle and roll angle of the unmanned floating machine using the inertial measurement unit,
    a horizontal-direction distance correcting step of correcting the horizontal distance information using the pitch angle and the roll angle acquired in the pitch angle and the roll angle acquiring step,
    a horizontal-direction distance acquiring step of acquiring distances between the inner wall surface of the structure and the unmanned floating machine in at least two different horizontal directions around the unmanned floating machine based on a yaw angle acquired by the inertial measurement unit, and
    a horizontal-direction current position information acquiring step of acquiring current position information in a horizontal direction from existing horizontal cross-sectional shape information of the structure.

2. The indoor monitoring system for a structure according to claim 1, wherein
    the flight position information acquisition unit is further configured to execute
    a height-direction distance measuring step of measuring distance information in any height direction between the unmanned floating machine and a top or a bottom of the structure using the distance measurement unit,
    a height-direction distance correcting step of correcting the distance information in the height direction using the pitch angle and the roll angle acquired in the pitch angle and the roll angle acquiring step, and
    a height-direction current position information acquiring step of acquiring current position information in the height direction from existing vertical cross-sectional shape information of the structure.

3. The indoor monitoring system for a structure according to claim 1, wherein
    multiple points are measured in the horizontal-direction distance measuring step and an averaged distance is used as the horizontal distance information.

4. The indoor monitoring system for a structure according to claim 2, wherein
    multiple points are measured in the height-direction distance measuring step and an averaged distance is used as the distance information in the height direction.

5. The indoor monitoring system for a structure according to claim 1, wherein
    the flight position information acquisition unit is mounted to the unmanned floating machine and transmits the acquired current position information to a ground side by a transmission unit to display the current position information on the monitor unit.

6. The indoor monitoring system for a structure according to claim 1, wherein
    the flight position information acquisition unit is mounted to a controller terminal on a ground side, and
    the information from the distance measurement unit and the information from the inertial measurement unit are transmitted to the ground side by a transmission unit and processed by the flight position information acquisition unit, and the current position information is displayed on the monitor unit.

7. The indoor monitoring system for a structure according to claim 1, wherein
    the imaging unit is any one or both of a still image imaging unit and a video imaging unit.

8. The indoor monitoring system for a structure according to claim 1, wherein
    a guard portion is provided around the unmanned floating machine.

9. An indoor monitoring method for a structure which uses an unmanned floating machine including a floating means which levitates the unmanned floating machine inside the structure by remote control, the method comprising:
- a distance measurement step executed in the unmanned floating machine and measuring a distance between the unmanned floating machine and an inner wall surface of the structure;
- an inertial measurement step executed in the unmanned floating machine and obtaining a pitch angle and a roll angle of the unmanned floating machine;
- an imaging step executed in the unmanned floating machine and imaging a structural body on the wall surface side of the structure;
- an operation step of remotely controlling the unmanned floating machine;
- a flight position information acquisition step of acquiring current position information of the unmanned floating machine based on information from the distance measurement step and information from the inertial measurement step; and
- a monitor displaying step of displaying image information from the imaging step and position information from the flight position information acquisition step,
- wherein in the flight position information acquisition step,
- a horizontal-direction distance measuring step of measuring horizontal distance information between the unmanned floating machine and the inner wall surface of the structure by the distance measurement step is executed,
- a pitch angle and a roll angle acquiring step of acquiring the pitch angle and the roll angle of the unmanned floating machine by the inertial measurement step is executed,
- a horizontal-direction distance correcting step of correcting the horizontal distance information using the pitch angle and the roll angle acquired in the pitch angle and the roll angle acquiring step is executed,
- a horizontal-direction distance acquiring step of acquiring distances between the inner wall surface of the structure and the unmanned floating machine in at least two different horizontal directions around the unmanned floating machine based on a yaw angle acquired in the inertial measurement step is executed, and
- a horizontal-direction current position information acquiring step of acquiring current position information in a horizontal direction from existing horizontal cross-sectional shape information of the structure is executed.

10. The indoor monitoring method for a structure according to claim 9, wherein
in the flight position information acquisition step,
- a height-direction distance measuring step of measuring distance information in any height direction between the unmanned floating machine and a top or a bottom of the structure by the distance measurement step is executed,
- a height-direction distance correcting step of correcting the distance information in the height direction using the pitch angle and the roll angle acquired in the pitch angle and the roll angle acquiring step, and
- a height-direction current position information acquiring step of acquiring current position information in the height direction from existing vertical cross-sectional shape information of the structure is executed.

11. The indoor monitoring method for a structure according to claim 9, wherein
multiple points are measured in the horizontal-direction distance measuring step and an averaged distance is used as the horizontal distance information.

12. The indoor monitoring method for a structure according to claim 10, wherein
multiple points are measured in the height-direction distance measuring step and an averaged distance is used as the distance information in the height direction.

13. The indoor monitoring method for a structure according to claim 9, wherein
the flight position information acquisition step is processed by the unmanned floating machine side to transmit the acquired current position information to a ground side to be monitor-displayed.

14. The indoor monitoring method for a structure according to claim 9, wherein
the flight position information acquisition step is processed by a ground side, and
the information from the distance measurement step and the information from the inertial measurement step are transmitted to the ground side and processed in the flight position information acquisition step, and the current position information is monitor-displayed.

15. The indoor monitoring method for a structure according to claim 9, wherein
the imaging step is any one or both of a still image imaging step and a video imaging step.

16. An indoor monitoring system for a structure comprising:
- an unmanned floating machine including a floating means which levitates the unmanned floating machine inside the structure by remote control;
- a distance measurement unit which is mounted to the unmanned floating machine and configured to measure a distance between the unmanned floating machine and an inner wall surface of the structure;
- an inertial measurement unit which is mounted to the unmanned floating machine and configured to obtain a pitch angle and a roll angle of the unmanned floating machine;
- an imaging unit which is mounted to the unmanned floating machine and configured to image a structural body on the wall surface side of the structure;
- an operation unit which is configured to remotely control the unmanned floating machine;
- a flight position information acquisition unit which is configured to acquire current position information of the unmanned floating machine based on information from the distance measurement unit and information from the inertial measurement unit; and
- a monitor unit which is configured to display image information from the imaging unit and position information from the flight position information acquisition unit,
- wherein the flight position information acquisition unit is further configured to execute
- a horizontal-direction distance measuring step of measuring horizontal distance information between the unmanned floating machine and the inner wall surface of the structure using the distance measurement unit, when the unmanned floating machine is controlled inside the structure by the remote control to turn along the inner wall surface of the structure after rising by a predetermined distance repeatedly till the unmanned floating machine arrives at a predetermined height,
- a pitch angle and a roll angle acquiring the pitch angle and the roll angle of the unmanned floating machine using the inertial measurement unit,
- a horizontal-direction distance correcting step of correcting the horizontal distance information using the pitch angle and the roll angle acquired in the pitch angle and the roll angle acquiring step, a horizontal-direction distance acquiring step of acquiring distances between the inner wall surface of the structure and the unmanned floating machine based on a yaw angle acquired by the inertial measurement unit, and a horizontal-direction current position information acquiring step of acquiring current position information in a horizontal direction from existing horizontal cross-sectional shape information of the structure.

17. An indoor monitoring method for a structure which uses an unmanned floating machine including a floating means which levitates the unmanned floating machine inside the structure by remote control, the method comprising:

a distance measurement step executed in the unmanned floating machine and measuring a distance between the unmanned floating machine and an inner wall surface of the structure;

an inertial measurement step executed in the unmanned floating machine and obtaining a pitch angle and a roll angle of the unmanned floating machine;

an imaging step executed in the unmanned floating machine and imaging a structural body on the wall surface side of the structure;

an operation step of remotely controlling the unmanned floating machine;

a flight position information acquisition step of acquiring current position information of the unmanned floating machine based on information from the distance measurement step and information from the inertial measurement step; and a monitor displaying step of displaying image information from the imaging step and position information from the flight position information acquisition step, wherein in the flight position information acquisition step, a horizontal-direction distance measuring step of measuring horizontal distance information between the unmanned floating machine and the inner wall surface of the structure is executed using the distance measurement step, when the unmanned floating machine is controlled inside the structure by the remote control to turn along the inner wall surface of the structure after rising by a predetermined distance repeatedly till the unmanned floating machine arrives at a predetermined height, a pitch angle and a roll angle acquiring step of acquiring the pitch angle and the roll angle of the unmanned floating machine is executed using the inertial measurement step, a horizontal-direction distance correcting step of correcting the horizontal distance information using the pitch angle and the roll angle acquired in the pitch angle and the roll angle acquiring step is executed, a horizontal-direction distance acquiring step of acquiring distances between the inner wall surface of the structure and the unmanned floating machine based on a yaw angle acquired in the inertial measurement step is executed, and a horizontal-direction current position information acquiring step of acquiring current position information in a horizontal direction from existing horizontal cross-sectional shape information of the structure is executed.

18. The indoor monitoring system for a structure according to claim 1, wherein the flight position information acquisition unit is further configured to execute an initial direction information acquiring step of acquiring initial direction information, obtained when the unmanned floating machine is positioned at the bottom of the inside of the structure.

19. The indoor monitoring system for a structure according to claim 1, wherein the structure is a boiler furnace and a stack.

20. The indoor monitoring system for a structure according to claim 1, wherein when the unmanned floating machine is introduced from an entrance of the structure, the operation unit is configured to remotely control the unmanned floating machine, (i) to raise by a predetermined distance inside the structure, (ii) to turn along inner surfaces of walls in four directions, (iii) to raise again by the predetermined distance, and (iv) to turn along the inner surfaces of the walls in the four directions the same manner to repeat the operations (i) to (iv) until the unmanned floating machine reaches a top of the structure, and to lower the unmanned floating machine.

* * * * *